United States Patent [19]
Kelman

[11] Patent Number: 4,833,890
[45] Date of Patent: May 30, 1989

[54] BIPARTITE INTRAOCULAR LENS

[76] Inventor: Charles D. Kelman, 269 Grand Central Pkwy., Floral Park, N.Y. 11005

[21] Appl. No.: 179,278

[22] Filed: Apr. 4, 1988

[51] Int. Cl.$^4$ ............................................. A61F 2/16
[52] U.S. Cl. ............................................. 623/6
[58] Field of Search ............................................. 623/6

[56] References Cited

U.S. PATENT DOCUMENTS

| | | | |
|---|---|---|---|
| 4,605,409 | 8/1986 | Kelman | 623/6 |
| 4,657,546 | 4/1987 | Shearing | 623/6 |
| 4,743,254 | 5/1988 | Davenport | 623/6 |

FOREIGN PATENT DOCUMENTS 3503690  11/1986  Fed. Rep. of Germany .......... 623/6

*Primary Examiner*—Ronald L. Frinks
*Attorney, Agent, or Firm*—Henry Sternberg; Bert J. Lewen

[57] ABSTRACT

Bipartite intraocular lens, insertable in temporarily contracted condition through a minimum size incision into the eye for implantation therein, including a haptic containing oblong lens body coactively mounted in a ring shaped, partially contractible, differential thickness, unitary tension frame formed of a tension band having light-masking contractible wings for inhibiting light rays directed toward the outer edge portions of the lens body from being scattered thereby toward the retina after the lens has been implanted in the eye.

17 Claims, 1 Drawing Sheet

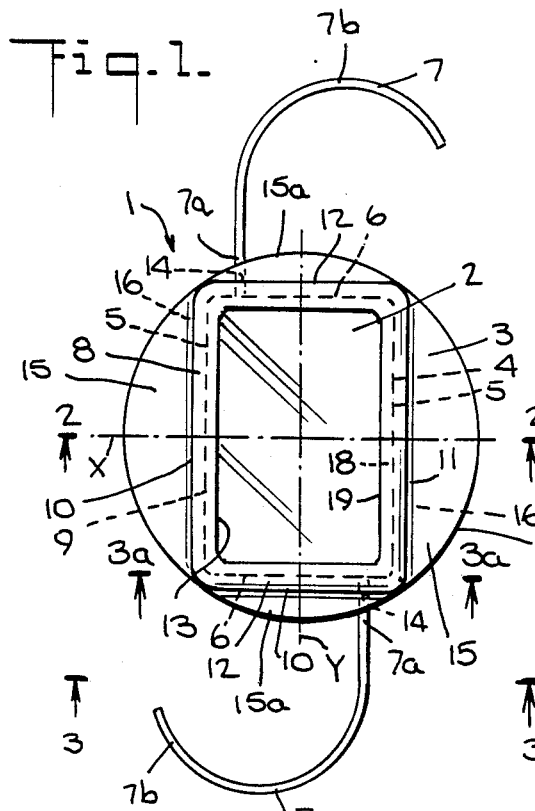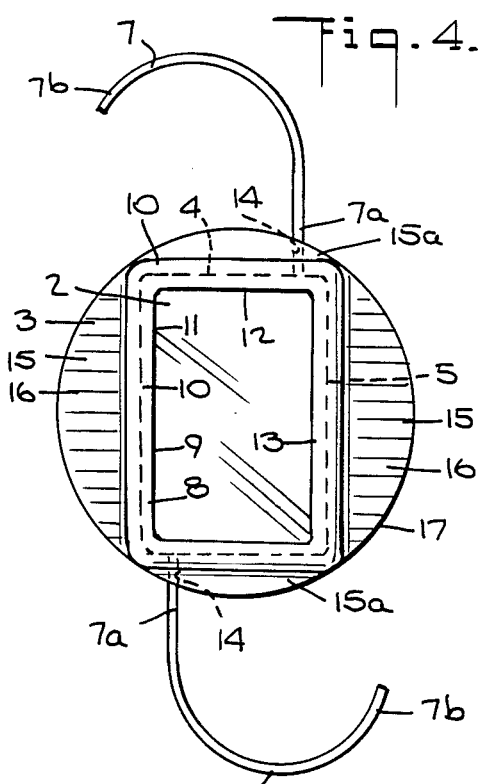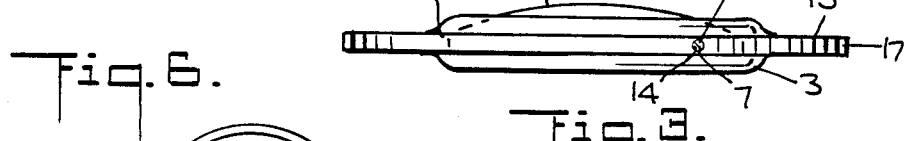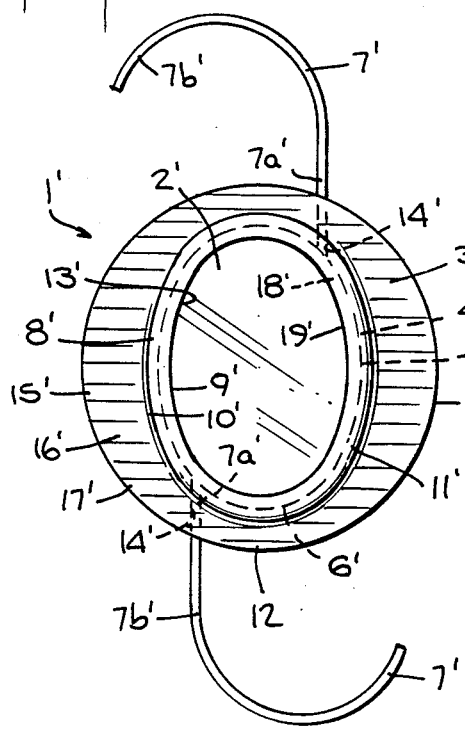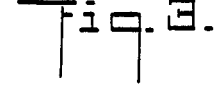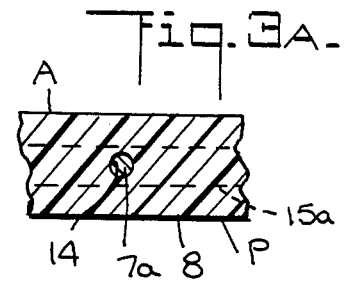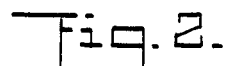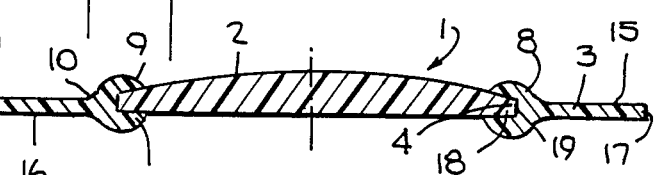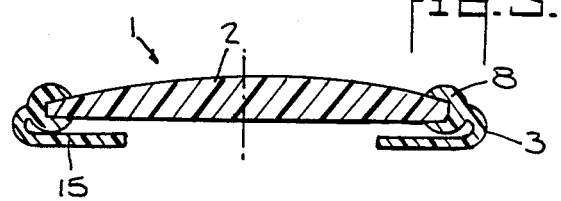

BIPARTITE INTRAOCULAR LENS

FIELD AND BACKGROUND OF THE INVENTION

The present invention relates to a bipartite intraocular lens, and more particularly to an artificial intraocular lens for implantation in an eye, such as in the posterior chamber, after extracapsular removal of the natural eye lens, that may be inserted through a minimum size incision into the eye, and that includes an oblong miniature lens body or optic, having position fixation means, e.g. haptics, which is coactively mounted in a ring shaped, partially contractible, differential thickness, unitary tension frame formed of a tension band and temporarily contractible wings, the wings having light-masking means for inhibiting light rays directed toward the outer edge portions of the lens body from being scattered thereby toward the retina after the lens has been implanted in the eye.

For treatment of conditions such as natural eye lens cataracts, a known eye surgery procedure is to remove the cataracted lens through a minimum size incision in the wall of the cornea of the eyeball, and replace it by an artificial intraocular lens as an internal implant lens. One specific surgical procedure involves the extracapsular removal of the natural eye lens, leaving portions of the posterior lens capsule intact to serve as a positioning site for the intraoculaar lens to be implanted in the eye.

U.S. Pat. No. 4,605,409 to Kelman discloses a one piece intraocular lens of the above type, having a small size, e.g. oblong, lens body or optic, flexible position fixation haptics, and deformable masking means, such as laterally disposed flat planar wings temporarily contracted to provide the lens with a reduced girth permitting insertion through such a minimum size corneal incision into an eye. Upon implantation, the wings mask the optic side edge portions to overcome the edge glare effect of otherwise scattered incoming light rays at the peripheral marginal regions of the small size lens, such light masking being achieved by leaving the wing surfaces in rough, unground, condition, or by providing an opaque coating thereon.

U.S. Pat. No. 4,168,547 to Konstantinov et al shows a grooved, circular intraocular lens received in a circular ring shaped thin haptic having five radially outwardly extending arms for mounting the lens across the iris in the anterior chamber of the eye. No light masking wings of the above type are present.

U.S. Pat. No. 4,450,593 to Poler etches a lens and haptic material laminate blank to form an array of individual modules, each comprising a circular lens prelaminated integrally to the inner edge of a circular ring shaped, fenestrated, web-like haptic, to provide intraocular and contact lens structures, by way of mass production technique. Each lens has a 6–9 mm diameter and each haptic has an outer diameter of up to 20 mm. No light masking wings of the above type are present.

It would be desirable to provide a minimum size intraocular lens for implantation in an eye, after extracapsular removal of the natural eye lens, permitting efficient insertion as an intact lens system through the same minimum size corneal incision used to remove the natural lens, and at the same time provide light-masking means for the lens body, while utilizing a structurally simple arrangement of parts, readily manufactured at relatively low cost from widely available materials.

SUMMARY OF THE INVENTION

It is among the objects of this invention to provide a bipartite artificial intraocular lens for insertion through a minimum size incision into an eye for implantation, e.g. after extracapsular removal of the natural eye lens, that includes a minimum width oblong lens body or optic having position fixation means, which is coactively mounted in a separate ring shaped, partially contractible, differential thickness, unitary tension frame having light-masking means for inhibiting light rays directed toward the outer edge of the optic from being scattered thereby toward the retina after lens implantation.

It is among the additional objects of this invention to provide a minimum insertion width bipartite lens permitting maximum accommodation of a small size optic mounted in a temporarily contractible, light-masking wing containing frame, through a minimum size eye incision, and which can be efficiently inserted intact into the eye and then implanted, and still provide light masking for the optic.

It is among the further objects of this invention to provide such a bipartite lens, which is readily manufactured at relatively low cost from widely available materials of desired characteristics, and which utilizes a structurally simple arrangement of cooperating parts.

According to this invention, a bipartite artificial intraocular lens is provided which is insertable in temporarily contracted condition through a minimum size incision into the eye for implantation therein, e.g. following extracapsular removal of the natural eye lens. The bipartite intraocular lens comprises an oblong lens body or optic, coactively mounted in a separate ring shaped, partially contractible, differential thickness, unitary tension frame.

The lens body has an outer edge defining two opposed longer sides and two opposed shorter sides, and position fixation means, e.g. haptics, having a neck portion fixedly connected to that outer edge and a cantilever portion extending outwardly from the neck portion for seating the lens in the eye.

The frame includes a relatively thick tension band having an inner edge and an outer edge and correspondingly defining two opposed longer sides and two opposed shorter sides, the inner edge forming an oblong aperture complemental to and which receives the lens body therein under tension. The band also has constrictive channel means which extend generally from the inner edge to the outer edge of the band and which locally embracively retain the adjacent neck portion of the position fixation means coactively therein.

The frame further includes two opposed, relatively thin, temporarily contractible, oblong planar wings, which define light-masking means, which extend outwardly from the outer edge of the band along the two longer sides thereof, and which are sized and shaped to provide the frame with a generally circular composite outer edge, the wings being temporarily contractible toward the lens body for insertion of the bipartite lens as an intact unit through a minimum size incision into the eye.

In particular, the frame is a continuous and uninterrupted ring shaped unitary member formed of an endless band integrally connected to the wings along their common extent and which fixedly mounts the lens body as a separate element therein.

Desirably, the band is slightly resiliently stretchable and the wings are resiliently locally flexible. The lens body may be made of shape retaining plastic and the frame of resiliently locally flexible and slightly resiliently stretchable plastic, with the wings being integrally connected to the band. The wing light-masking means may comprise optically opaque means or optically translucent means.

The position fixation means may be in the form of two opposed haptics, each having a neck portion and a cantilever portion, with the neck portions integrally connected correspondingly to the two shorter sides of the lens body, and the channel means may be in the form of two correspondingly opposed through bores locally embracively retaining the adjacent neck portions of the haptics therein. Preferably, the haptic neck portions and band through bores are of complemental size and cross sectional shape, and the neck portions are in substantially coextensive abutting contact with the adjacent surfaces of the through bores.

The lens body outer edge and band inner edge advantageously have coacting seating formations for retaining the lens body in the aperture, such as a groove in the band inner edge and a groove engaging peripheral portion at the lens body outer edge.

According to a preferred embodiment, the lens body has a maximum dimension in its oblong width direction of about 3 mm, the frame has a maximum annular dimension in its oblong width direction of about 2 mm, the band has a thickness of about 1.5-2 mm, the channel means and adjacent neck portion of the position fixation means have complemental diameters of about 0.2 mm, the wings have a thickness of about 0.25-0.5 mm, the band has an annular dimension extending from its inner edge to its outer edge of about 0.25 mm, and the wings have a maximum dimension in the oblong width direction of about 1.75 mm.

In one preferred form, the lens body has a generally rectangular shape and each wing has the shape of a segment of a circle whose chord is defined by a corresponding longer side of the band. In another such form, the lens body has a generally oval or elliptical shape and each wing has the shape of a convexo-concave crescent with a convex side defined by a portion of the circular outer edge of the frame and a concave side defined by a corresponding longer side of the band.

BRIEF DESCRIPTION OF THE DRAWINGS

Other objects of the invention will become apparent from the within specification and accompanying drawings, in which:

FIG. 1 is a plan view of the front or anterior side of the bipartite intraocular lens according to a generally rectangularly shaped oblong lens body embodiment of the invention;

FIG. 2 is a sectional view taken along line 2—2 of FIG. 1, showing the manner in which the lens body is retained in the frame;

FIG. 3 is an end view taken along the line 3—3 of FIG. 1, showing the manner in which the channel means receives the adjacent neck portion of the corresponding lens body haptic;

FIG. 3a is an enlarged sectional partial view, similar to FIG. 3, but taken along the line 3a—3a of FIG. 1;

FIG. 4 is a plan view of the rear or posterior side of the lens of FIG. 1, showing translucent surfaces on the wing undersides for rendering the wings translucent;

FIG. 5 is a view similar to FIG. 2, showing the manner in which the wings are temporarily contracted toward the lens body for insertion of the lens through a minimum size incision into the eye; and FIG. 6 is a plan view showing the rear or posterior side of a bipartite intraocular lens according to a generally oval or elliptically shaped oblong lens body embodiment herein.

DESCRIPTION OF THE PREFERRED EMBODIMENTS

Referring to the drawings, and initially to FIGS. 1-3, an artificial bipartite intraocular lens 1 according to one embodiment of the invention is shown, formed by an oblong lens body or optic 2 of generally rectangular shape coactively mounted in a separate continuous and uninterrupted ring shaped, partially contractible, differential thickness, unitary tension frame 3, to provide an intact two piece assembly which is insertable as a unit in temporarily contracted condition through a minimum size incision into the eye for implantation therein.

Optic 2 has an outer boundary edge 4 which defines two opposed longer sides 5,5 and two opposed shorter sides 6,6, and a selective curvature profile (FIGS. 2-3) for providing the desired optical refractive characteristics for the lens. Optic 2 is advantageously provided with position fixation means such as the diametrically opposed haptics 7,7, e.g. of limited flexibility, having neck portions 7a,7a fixedly connected to edge 4 and cantilever portions 7b,7b extending outwardly from neck portions 7a,7a for seating lens 1 in the eye. In particular, the neck portion 7a of one haptic 7 is connected to optic 2 at one point on one shorter side 6, and the neck portion 7a of the other haptic 7 is connected to optic 2 at a diagonally opposite point on the other shorter side 6, preferably by integral connections.

Frame 3 includes a relatively axially thick or bulbous tension band 8, e.g. as an endless or continuous and uninterrupted ring shaped "elastic band", having an inner edge 9 and an outer edge 10 and correspondingly defining two opposed longer sides 11,11 and two opposed shorter sides 12,12, with inner edge 9 forming an oblong central aperture 13 of generally rectangular shape, complemental to and receiving optic 2 under tension.

Band 8 is particularly provided with constrictive channel means such as diagonally opposed through bores 14,14, which extend generally from inner edge 9 to outer edge 10 and which are located so as to retain, locally embracively, the adjacent neck portions 7a,7a of the position fixation means or haptics 7,7 therein, through bores 14 respectively coinciding with the positions of such haptics 7 on optic 2.

Specifically, as shown more clearly in FIG. 3a, haptic neck portions 7a and band through bores 14 are desirably of complemental diametrical size and cross sectional shape, such that each neck portion 7a is in substantially coextensive abutting contact with the adjacent interior surface of its associated through bore 14, thereby forming a relatively stable, reinforcing interconnection between these parts at balanced, i.e. diametrically opposed, sites relative to the periphery of lens 1.

The channel means, advantageously constructed as through bores 14 which coact with haptic neck portions 7a, thus serve to stabilize the disposition of optic 2 in frame 3, and prevent relative rotational displacement, as well as relative axial displacement, between optic 2 and band 8.

Frame 3 further includes two opposed, relatively thin, temporarily contractible or foldable longer side oblong planar wings 15,15, which define light-masking means 16,16, such as by providing wings 15,15 as opaque or translucent members, or by providing them with opaque or translucent surface areas, as shown in FIG. 4 on the undersides of the wings, i.e. on the posterior side of frame 3. Wings 15,15 extend generally outwardly from outer edge 10 along the two opposed longer sides 11,11 of band 8, and are sized and shaped to provide frame 3 with a generally circular composite outer border edge 17. Wings 15 are coextensively, preferably integrally, connected to band 8 along the longer sides 11 at outer edge 10.

As shown in FIG. 5, wings 15 are temporarily contractible or foldable toward and partially across optic 2 for insertion of lens 1 in minimum width girth condition through a minimum size incision into the eye.

Optionally, to achieve a more fully rounded circular configuration, band outer edge 10 may be provided, e.g. integrally, along shorter sides 12,12 with similar top and bottom minor size wings 15a,15a (FIG. 1), although these additions are not particularly important since the light masking wings 15,15 serve the desired function along the longer sides of optic 2 where such function is of major significance.

However, even where these optional top and bottom wings 15a are present, their thickness dimension will be sufficient to contain the outer or extension portions of through bores 14 therein for insertion of haptics 7 therethrough, especially since the retention of neck portions 7a is accomplished effectively by the main portions of through bores 14 in band 8, without reference to the presence or absence of top and bottom minor size wings 15a, or any extension portions of through bores 14 therein (see FIG. 3a).

Outer edge 4 of optic 2 and inner edge 9 of band 8 suitably have coacting seating formations, such as an internal peripheral groove 19 in inner edge 9 and a groove engaging peripheral portion or extension 18 at the lens body outer edge 4, for retaining optic 2 in aperture 13. This arrangement particularly permits optic 2 to be permanently received in band 8 of frame 3 during manufacture of bipartite lens 1.

Indeed, in assembling optic 2 and frame 3 during manufacture, normally one haptic 7 will be inserted into and threaded or "snaked" through its associated through bore 14 until the neck portion 7a thereof is seated as fully as possible in that through bore, followed by like insertion and threading or "snaking" of the opposite haptic 7 through its associated through bore 14, whereupon final alignment of optic 2 relative to band 8 will be undertaken and in turn pressing of optic 2 into aperture 13 via coaction between band groove 19 and optic peripheral portion 18 while slightly distending or stretching band 8 for "snap in" action.

The resulting two piece assembly of lens 1 thus constitutes a continuous and uninterrupted ring shaped unitary frame 3, including an endless apertured band 8 integrally connected to temporarily inwardly or medially contractible or foldable, i.e. collapsible, side wings 15, and a separate miniature optic 2 fixedly mounted in the band aperture.

Necessarily, the dimensions of optic 2 and aperture 13 will be precisely selected and conformed with each other to assure that optic 2 will be "snapped" into aperture 13 and held in place in frame 3 under slight tension by the "tension" or "rubber band" action of band 8. At the same time, wings 15 will necessarily be more or less self-collapsibly deformable or foldable to assure the temporary contracting thereof inwardly or medially along or across the adjacent outer portions of optic 2 at longer sides 5, as shown in FIG. 5, for insertion of lens 1 through the minimum size corneal incision.

It will be noted that, in conjunction with the effective seating of optic 2 via haptics 7 as position fixation means in the eye, e.g. in the posterior chamber remaining after extra-capsular removal of the natural eye lens by the surgeon, the reinforcing embracive action of through bores 14 on haptic neck portions 7a will inherently contribute to the stable positioning of lens 1 in place.

In accordance with one well known surgical procedure, for example, the surgeon will remove the natural lens and a portion of the anterior wall part of the natural lens capsule via the usual small size corneal incision, e.g. 3.5 mm, leaving intact the posterior wall part of the lens capsule, which is held in place by the zonules or suspensory ligament and fibers attached to its external periphery. The internal periphery of the posterior wall part forms a recessed anterior cul-de-sac or ciliary sulcus which efficiently serves as a posterior chamber seating location for the haptics of the lens.

In the usual way, one haptic 7 may be positioned in its desired location, e.g. in the posterior chamber, to stabilize lens 1, followed by the other haptic 7 in its desired location, e.g. also in the posterior chamber, after which wings 15 may be optionally slightly pressed against the adjacent portions of the eye thereat, whereby to complete the lens implantation.

Of course, by reason of the nesting coaction provided by optic peripheral portion 18 and band groove 19, as well as the locally embracive retaining of the haptic neck portions 7a,7a by the constrictive through bores 14,14, optic 2 will be retained against displacement out of aperture 13, so as to assure positive resilient interconnection of these parts, once haptics 7 have been inserted into and "snaked" through the through bores 14,14 and in turn optic 2 has been "snapped" into aperture 13 against the reserve tension of band 8 as provided by its slightly resiliently stretchable nature.

The minimum shorter side girth of bipartite lens 1 facilitates exploitation of the minimum size corneal incision used by the surgeon for extracapsular removal of the natural eye lens, since upon contracting wings 15 lens 1 may be efficiently inserted as an intact unit through that same minimum size incision into the eye. This is particularly significant since, understandably, the smaller the size of the corneal incision the less the trauma experienced by the patient, and in turn the less the pain and discomfort endured then and thereafter, not only due to the incision itself but also the number and/or size of any needed sutures.

Thus, because wings 15 are made of deformable or foldable material, they may be simply folded or contracted onto the adjacent outer portions of optic 2, as shown in FIG. 5, or the like, to provide a minimum girth compact unit readily longitudinally insertable through that same minimum size incision. Since such minimum girth is only limited by the width of the oblong shaped miniature optic 2, that optic width may be conveniently conformed to the size of that incision.

The deformable nature of wings 15 is effectively enhanced by providing these parts of locally flexible material, and the tension embracing of optic 2 by band 8 is likewise effectively enhanced by providing band 8 of slightly resiliently stretchable material. These contemplated characteristics are achieved by making wings 15 of minimum cross sectional thickness, and using polymethylmethacrylate (PMMA) or similar shape retaining plastic material for optic 2, and silicone or similar limitedly resilient yet flexible plastic material for band 8 and wings 15, while precisely determining the dimensions of optic 2 and aperture 13 to assure that optic 2 will be held in frame 3 by band 8 under slight resilient tension.

While optic 2 is preferably made of rigid polymethylmethacrylate (PMMA) so that it may be readily "snapped" into position, haptics 7 are conveniently made of suitable shape retaining, yet optionally limitedly resilient or flexible, plastic material such as a suitable polymethylmethacrylate (PMMA), although they may also be made of polypropylene or silicone plastic should enhanced deformable characteristics for these parts be especially desired.

Of course, the optic will be formed of suitable light focusing material having the desired optical characteristics, and all materials used for the bipartite lens must be compatible with the eye fluid environment in the interior of the eyeball, and thus be non-toxic. After the lens is inserted and implanted by the surgeon, the intact assembly will advantageously retain its desired optical and other characteristics.

Favorably, optic 2 has a maximum dimension in the oblong width direction thereof of about 3 mm, and frame 3 has a maximum annular dimension in the oblong width direction thereof of about 2 mm, such that band 8 has an annular dimension extending from its inner edge 9 to its outer edge 10 of about 0.25 mm and wings 15 each have a maximum dimension in the oblong width direction thereof of about 1.75 mm, whereby lens 1 has a diameter of about 7 mm in normal uncontracted condition.

These dimensions are readily accommodated in a minimum size corneal incision of for instance about 3.5 mm, because of the temporarily contractible nature of wings 15 and which is enhanced by the differential thickness nature of frame 3.

Specifically, while bulbous band 8 favorably has a thickness of about 1.5 to 2 mm to assure proper accommodation of optic 2 in aperture 13, and especially the thickness expanse needed to accommodate band groove 19 for coaction with optic peripheral portion 18, on the other hand wings 15 desirably have a common thickness of only about 0.25 to 0.5 mm to assure ready deformation or folding thereof along their coextensive connections to longer sides 11 of band 8 for achieving temporary contracting of wings 15 for the underlying purpose.

Thus, as may be appreciated from FIG. 1, circular outer edge 17 of frame 3 preferably has a diameter of about 7 mm, which is generally considered the proper average size for an intraocular lens, and wings 15 have a maximum width at their widest crest portions of about 1.75 mm, so as to provide the approximately 0.25 mm annular width band 8 with a central aperture 13 having an oblong shorter side width of about 3 mm, i.e. along the horizontal axis X, and an oblong longer side length of about 5.5 to 6 mm, i.e. along the vertical axis Y.

In turn, the miniature optic 2 will have the same dimensions as aperture 13, i.e. an oblong shorter side width of about 3 mm and an oblong longer side length of about 5.5 to 6 mm, thereby assuring the tension held disposition of optic 2 in band 8 of frame 3. The height or thickness of optic 2, i.e. along transverse optical axis Z (FIG. 2), will depend on the selected optical characteristics of optic 2. Nevertheless, as may be seen from FIGS. 2–3, wings 15 are generally of thin, flat profile in cross section as compared to the thickened conventional size rounded curvature profile cross section of optic 2, e.g. with such optic having a maximum central thickness dimension of about 1.5 mm and a maximum peripheral thickness dimension of about 1 mm at edge 4, i.e. in the direction of transverse optical axis Z.

As may be appreciated from FIG. 3a, the open cross sectional area of through bores 14 is generally at most about 20% of the total corresponding cross sectional thickness area of band 8, i.e. extending from the anterior side A to the posterior side P thereof, whereas the length of through bores 14 is generally at least abouttwo times the diameter of the through bores. Thus, the provision for through bores 14 in band 8 achieves the desired embracive accommodation of haptics 7 therein without significant decrease in the structural integrity and tensile strength of the mass in the corresponding cross sectional area surrounding through bores 14.

In line with the foregoing dimensions, through bores 14 and haptic neck portions 7a may have complemental diameters of about 0.2 mm, while optional top and bottom minor wings 15a, like major wings 15, may have a thickness of about 0.25—0.5 mm (cf. FIG. 3a).

In terms of the geometrical shape of the rectangular embodiment per optic 2 and frame 3, it will be seen that wings 15 form opposed longitudinal members, each of which has the shape of a segment of the circle bounded by circular outer edge 17, whose chord is defined by a corresponding longer side 11 of band 8. Where opposed top and bottom wings 15a are optionally present, they will form similar segment shaped regions bounded by outer edge 17 of that circle. Also, the arrangement is such that a diametrically symmetrical configuration is provided for the opposed haptics 7 on optic 2, i.e. with their curves extending in opposite directions.

FIG. 6 shows an alternative embodiment of a bipartite intraocular lens 1' in which prime (') designations are assigned to analogous parts to those shown in FIGS. 1–5, here used to illustrate an oblong generally oval or elliptically shaped lens body or optic 2' and associated partially contractible frame 3' having an oblong generally oval or elliptically shaped band 8' with a central aperture 13' of like shape, bounded on longer sides 11' by temporarily contractible wings 15' coextensively integrally connected thereto, each having the shape of a convexo-concave crescent, with a convex outer side defined by a portion of circular outer edge 17' of frame 3', and a concave inner side defined by a corresponding longer side 11' of band 8'.

Thus, the bipartite lens assembly of each embodiment of the invention constitutes a structurally simple arrangement of cooperating parts forming an intact coactively mounted assembly which is readily manufactured at relatively low cost from widely available materials of desired characteristics.

The lens is manufactured, for instance, by first making a miniature generally rectangular or oval optic, e.g. of PMMA or the like, and providing diametrically opposed haptics, e.g. of PMMA, polyethylene, silicone or the like, in fixed connection with the optic along the shorter sides thereof, and then forming a side wing containing outer ring member or tension frame of resilient material, e.g. silicone or the like, having a thickened inner portion or band surrounding a central opening or aperture conforming in shape to but slightly smaller than the peripheral dimensions of the optic, plus diametrically opposed through bores aligned for the haptic neck portions.

Hence, when these two parts are assembled, the optic is securely received in the aperture, and the haptic neck portions are locally embracively retained in the through bores, i.e. upon "snaking" the haptics through the through bores and "snapping" the optic into the aperture.

The thickened inner portion of the outer ring member or frame affirmatively acts as a rubber band tightly to engage the optic and its haptics, and to maintain such engaged condition during insertion of the resulting bipartite lens into the eye and thereafter. Indeed, the construction is such as to insure that the miniature optic is tightly held in place by this rubber band like action even upon folding deformation of the thin flange like wings of the ring member or frame for insertion of the lens through a minimum size incision in the eye.

In each embodiment hereof, whereas the thickened band is desirable slightly resiliently stretchable, so as to act as a rubber band surrounding and fixedly retaining the miniature optic, the wings are resiliently locally flexible, yet despite their relative thinness to achieve enhanced foldability they also effectively serve as basic light-masking means by reason of their opaque or translucent character.

It will be understood that the surgical procedures contemplated herein are well known to those skilled in the art, and that the nature and significance of the masking means as they relate to the small size optics used herein are the same as described more fully in the aforesaid U.S. Pat. No. 4,605,409.

It will be appreciated that the foregoing specification and accompanying drawings are set forth by way of illustration and not limitation of the present invention, and that various modifications and changes may be made therein without departing from the spirit and scope of the present invention which is to be limited solely by the scope of the appended claims.

What is claimed is:

1. Bipartite intraocular lens, insertable in temporarily contracted condition through a minimum size incision into the eye for implantation therein, which comprises
   an oblong lens body coactively mounted in a ring shaped, partially contractible, differential thickness, unitary tension frame,
   the lens body having an outer edge defining two opposed longer sides and two opposed shorter sides, and position fixation means having a neck portion fixedly connected to said edge and a cantilever portion extending outwardly from said neck portion for seating the lens in the eye,
   the frame including a relatively thick tension band having an inner edge and an outer edge and correspondingly defining two opposed longer sides and two opposed shorter sides, the inner edge forming an oblong aperture complemental to and receiving the lens body therein under tension, and the band further having constrictive channel means extending generally from the inner edge to the outer edge thereof and locally embracively retaining the adjacent neck portion of the position fixation means coactively therein, and
   the frame further including two opposed, relatively thin, temporarily contractible, oblong planar wings, defining light-masking means and extending outwardly from the outer edge of the band along the two longer sides thereof, and sized and shaped to provide the frame with a generally circular composite outer edge, the wings being temporarily contractible toward the lens body for insertion of the lens through a minimum size incision into the eye.

2. Lens of claim 1 wherein the band is slightly resiliently stretchable and the wings are resiliently locally flexible.

3. Lens of claim 1 wherein the channel means are in the form of a through bore.

4. Lens of claim 1 wherein the position fixation means are in the form of two opposed haptics, each having a neck portion and a cantilever portion, with the neck portions integrally connected correspondingly to the two shorter sides of the lens body, and the channel means are in the form of two correspondingly opposed through bores locally embracively retaining the adjacent neck portions of the haptics therein.

5. Lens of claim 4 wherein the haptic neck portions and band through bores are of complemental size and cross sectional shape, and the neck portions are in substantially coextensive abutting contact with the adjacent surfaces of the through bores.

6. Lens of claim 1 wherein the lens body outer edge and band inner edge are provided with coacting seating formations for retaining the lens body in the aperture.

7. Lens of claim 6 wherein the formations include a groove in said band inner edge and a groove engaging peripheral portion at said lens body outer edge.

8. Lens of claim 1 wherein the wing light-masking means comprise optically opaque means.

9. Lens of claim 1 wherein the wing light-masking means comprise optically translucent means.

10. Lens of claim 1 wherein the lens body has a maximum dimension in the oblong width direction thereof of about 3 mm, and the frame has a maximum annular dimension in the oblong width direction thereof of about 2 mm.

11. Lens of claim 10 wherein the band has a thickness of about 1.5-2 mm, the channel means and adjacent neck portion of the position fixation means have complemental diameters of about 0.2 mm, and the wings have a thickness of about 0.25-0.5 mm.

12. Lens of claim 11 wherein the band has an annular dimension extending from its inner edge to its outer edge of about 0.25 mm and the wings have a maximum dimension in the oblong width direction of about 1.75 mm.

13. Lens of claim 1 wherein the lens body is made of shape retaining plastic and the frame is made of resiliently locally flexible and slightly resiliently stretchable plastic, the wings being integrally connected to the band.

14. Lens of claim 1 wherein the lens body has a generally rectangular shape and the wings each have the shape of a segment of a circle whose chord is defined by a corresponding longer side of the band.

15. Lens of claim 1 wherein the lens body has a generally elliptical shape and the wings each have the shape of a convexo-concave crescent with a convex side defined by a portion of the circular outer edge of the frame and a concave side defined by a corresponding longer side of the band.

16. Bipartite intraocular lens, insertable in temporarily contracted condition through a minimum size incision into the eye for implantation therein, which comprises an oblong lens body coactively mounted in a ring shaped, partially contractible, differential thickness, unitary tension frame, the lens body having an outer edge defining two opposed longer sides and two opposed shorter sides, and two opposed haptics each having a neck portion integrally connected to said edge, correspondingly at the two shorter sides of the lens body, and a cantilever portion extending outwardly from said neck portion for seating the lens in the eye, the frame being in the form of a continuous and uninterrupted ring shaped unitary member including a relatively thick endless, slightly resiliently stretchable, tension band having an inner edge and an outer edge and correspondingly defining two opposed longer sides and two opposed shorter sides, the inner edge forming an oblong aperture complemental to and receiving the lens body therein under tension, and the band further having two opposed constrictive through bores extending from the inner edge to the outer edge thereof, correspondingly at the two shorter sides of the band, the neck portions of the haptics and through bores of the band being of complemental size and cross sectional shape, and the through bores locally embracively retaining the adjacent haptic neck portions coactively therein such that the neck portions are in substantially coextensive abutting contact with the adjacent surfaces of the through bores, the frame thereby fixedly mounting the lens body as a separate element therein so as to provide the bipartite intraocular lens, and the frame further including two opposed, relatively thin, resiliently locally flexible, temporarily contractible, oblong planar wings, defining masking means integrally connected to and extending outwardly from the outer edge of the band along the two longer sides thereof, and sized and shaped to provide the frame with a generally circular composite edge, the wings being temporarily contractible toward the lens body for insertion of the lens through a minimum size incision into the eye.

17. Lens of claim 16 wherein the band inner edge is provided with a groove and the lens body outer edge is provided with a groove engaging peripheral portion for seating the lens body in the band groove for retaining the lens body in the aperture.

* * * * *